(12) United States Patent
Jiang et al.

(10) Patent No.: US 9,155,787 B2
(45) Date of Patent: *Oct. 13, 2015

(54) METHODS OF PREVENTING REJECTION OF TRANSPLANTED TISSUE BY ADMINISTERING ANTI-CD40L ANTIBODY AND DENDRITIC CELLS LOADED WITH TYPE B PEPTIDE

(71) Applicant: THE TRUSTEES OF COLUMBIA UNIVERSITY IN THE CITY OF NEW YORK, New York, NY (US)

(72) Inventors: Hong Jiang, Fort Lee, NJ (US); Leonard Chess, Scarsdale, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/540,452

(22) Filed: Nov. 13, 2014

(65) Prior Publication Data
US 2015/0110813 A1 Apr. 23, 2015

Related U.S. Application Data

(63) Continuation of application No. 13/144,579, filed as application No. PCT/US2010/000409 on Feb. 9, 2010, now Pat. No. 8,911,739.

(60) Provisional application No. 61/276,738, filed on Sep. 15, 2009, provisional application No. 61/207,352, filed on Feb. 10, 2009.

(51) Int. Cl.
| | | |
|---|---|---|
| A61K 39/395 | (2006.01) | |
| C12N 5/10 | (2006.01) | |
| A61K 38/17 | (2006.01) | |
| A61K 39/00 | (2006.01) | |
| A61K 45/06 | (2006.01) | |
| C07K 16/28 | (2006.01) | |
| A61K 35/15 | (2015.01) | |

(52) U.S. Cl.
CPC ............ *A61K 39/001* (2013.01); *A61K 35/15* (2013.01); *A61K 38/1709* (2013.01); *A61K 39/3955* (2013.01); *A61K 45/06* (2013.01); *C07K 16/2875* (2013.01); *A61K 2039/5154* (2013.01); *A61K 2039/545* (2013.01); *A61K 2039/577* (2013.01)

(58) Field of Classification Search
None
See application file for complete search history.

(56) References Cited

U.S. PATENT DOCUMENTS 8,911,739 B2 * 12/2014 Jiang et al. ............... 424/154.1

OTHER PUBLICATIONS

Hong Jiang Declaration under 37 CFR 1.132 submitted Sep. 13, 2013 in U.S. Appl. No. 13/144,579.*

* cited by examiner

*Primary Examiner* — Phillip Gambel
(74) *Attorney, Agent, or Firm* — Ascenda Law Group PC

(57) ABSTRACT

A method is provided for preventing rejection by an immune system of a recipient subject of a tissue transplanted from a donor subject into the recipient subject without the need for long-term administration of non-specific immunosuppressive drugs.

13 Claims, 1 Drawing Sheet

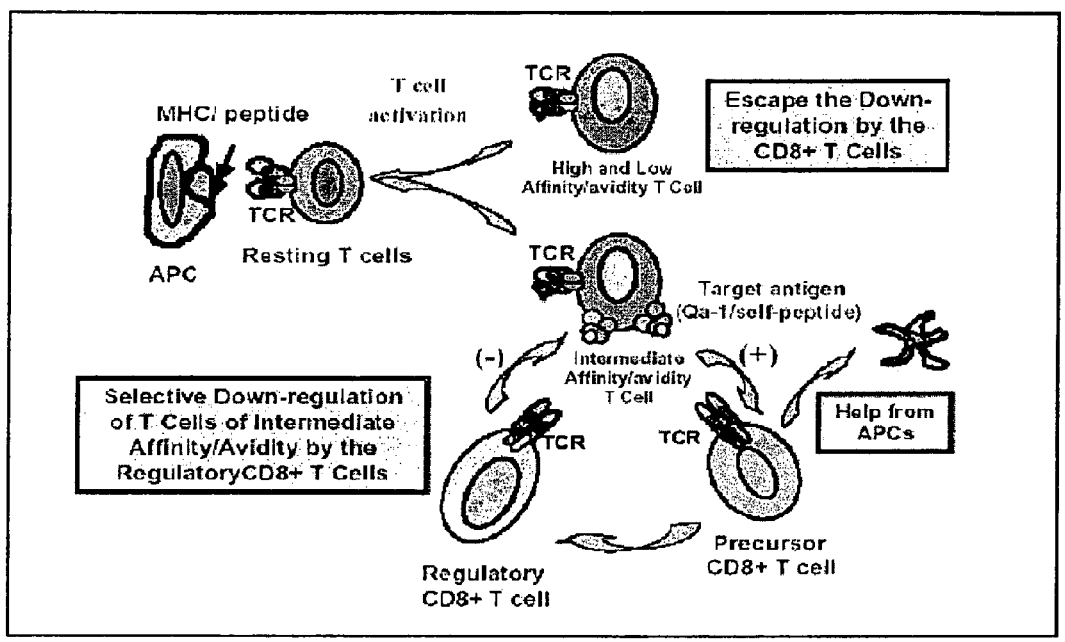

SEQUENCE LISTING

```
<160> NUMBER OF SEQ ID NOS: 3

<210> SEQ ID NO 1
<211> LENGTH: 9
<212> TYPE: PRT
<213> ORGANISM: Artificial Sequence
<220> FEATURE:
<223> OTHER INFORMATION: chemically synthesized sequence
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (2)..(2)
<223> OTHER INFORMATION: Xaa = Met or Leu
<220> FEATURE:
<221> NAME/KEY: MISC_FEATURE
<222> LOCATION: (3)..(8)
<223> OTHER INFORMATION: Xaa = any amino acid

<400> SEQUENCE: 1

Xaa Xaa Xaa Xaa Xaa Xaa Xaa Xaa Leu
1               5

<210> SEQ ID NO 2
<211> LENGTH: 9
<212> TYPE: PRT
<213> ORGANISM: Murine Sp.

<400> SEQUENCE: 2
```

```
Gln Met Arg Pro Val Ser Arg Ala Leu
1               5

<210> SEQ ID NO 3
<211> LENGTH: 9
<212> TYPE: PRT
<213> ORGANISM: Homo sapiens

<400> SEQUENCE: 3

Gln Met Arg Pro Val Ser Arg Val Leu
1               5
```

METHODS OF PREVENTING REJECTION OF TRANSPLANTED TISSUE BY ADMINISTERING ANTI-CD40L ANTIBODY AND DENDRITIC CELLS LOADED WITH TYPE B PEPTIDE

CROSS-REFERENCE TO RELATED APPLICATIONS

This application is a continuation of U.S. application Ser. No. 13/144,579, filed Sep. 13, 2011, now U.S. Pat. No. 8,911,739 (issued Dec. 16, 2014), which is a national stage under 35 U.S.C. 371 based on and claiming the benefit of International Application PCT/US2010/00409, filed on Feb. 9, 2010, which claims the benefit of priority from U.S. Provisional Application No. 61/276,738, filed on Sep. 15, 2009 and U.S. Provisional Application No. 61/207,352, filed on Feb. 10, 2009, the entire contents of each of which are incorporated herein by reference.

Throughout this application, various publications are referenced in parentheses by number. Citations for these references may be found at the end of the specification immediately preceding the claims. The disclosures of these publications in their entireties are hereby incorporated by reference into this application to more fully describe the state of the art to which this invention pertains.

The work disclosed herein was made with government support under grant no. U19 AI46132 from the National Institutes of Health. Accordingly, the U.S. Government has certain rights in this invention.

INCORPORATION-BY-REFERENCE OF SEQUENCE LISTING

A sequence listing, filed as the ASCII text file "4361-003-US-CON_Sequence_Listing.txt" having a file size of 2 kilobytes, is incorporated herein by reference in its entirety.

BACKGROUND

Normal function against infectious agents is based on how the immune system achieves self/non-self discrimination, which remains a central conundrum in Immunology (1). What is "self" and what is "foreign", as seen by the immune system, determines how the immune system discriminates self from non-self. In this regard, the pioneering work of Burnet and Medawar suggested that the definition of self versus non-self is arbitrary to the immune system because foreign antigens presented during fetal life are thereafter considered self (2, 3). Moreover, it is known that all T cells are selfreferential in the sense that they are positively selected for survival on self-peptide/s bound to MHC molecules during thymic positive selection (4-7) before thymic negative selection, in which thymocytes expressing TCR of high avidity to the majority of self-antigens are deleted (8-10).

It is generally accepted that thymic negative selection eliminates the "imminent danger" of pathogenic autoimmunity in the periphery and is the major mechanism of self-tolerance. However, while releasing the "innocent" self-reactive T cells with low avidity, thymic negative selection also allows a large fraction of self-reactive T cells with "higher" or "intermediate" avidity to be released into the periphery under normal circumstances (11-13). The existence of the "intermediate avidity" self-reactive T cells in the periphery represents a "potential danger" of pathogenic auto-immunity inherited in each individual because these T cells can often be activated when they encounter self-peptides presented at a sufficient level and some may differentiate into potentially pathogenic effector cells to initiate an autoimmune disease (13-16). Self/non-self discrimination must continue in the periphery after thymic negative selection and one of the major functions of peripheral regulatory mechanisms is to selectively down-regulate immune responses to self-antigens without damaging the normal responses to foreign pathogens to maintain self-tolerance (17).

How does the immune system discriminate self from non-self in the periphery? Since self/non-self discrimination initiated during thymic negative selection is based on the avidity of thymocyte activation (8-10) and a large fraction of self-reactive T cells escape thymic negative selection (11-13), it is crucial to understand how the resultant peripheral T cell repertoire is regulated to complete self non-self discrimination initiated by thymic negative selection in order to maintain self-tolerance. In this regard, we have proposed and tested an "Avidity Model of Peripheral T Cell Regulation" in which self non-self discrimination can be achieved in the periphery via selective down-regulation of intermediate avidity T cells, to both self and foreign antigens, by Qa-1/HLA-E restricted CD8+ T cells (18, 19). Since the potentially pathogenic self-reactive T cells are included in the intermediate avidity T cell pool, selective down-regulation of intermediate avidity T cells can directly control autoimmune disease. On the other hand, the unified mechanism of selective down-regulation of intermediate avidity T cells does not inhibit immunity largely to foreign infectious agents or alloantigens mediated by high avidity T cells, simply because the high avidity T cells are not subject to this down-regulation. Thus, by a unified and simple mechanism, the immune system could accomplish self non-self discrimination in the periphery to specifically maintain self-tolerance without paying the price of dampening anti-infection and anti-tumor immunity.

The concept that perceiving the avidity of T cell activation can be translated into peripheral T cell regulation is the essence of the "Avidity Model". The cellular mechanism that defines how perceiving the avidity of T cell activation is translated into peripheral T cell regulation and the molecular structures recognized by regulatory T cells that enable them to discriminate self from non-self in the periphery are the key issues of the regulatory T cell biology. In this regard a surrogate target structure (Qa-1/Hsp60sp) was recently identified which is specifically recognized by the Qa-1 restricted CD8+ T cells (1). The common surrogate target structure, the Qa-1/Hsp60sp complex, is only preferentially expressed at a higher level on the intermediate, but not high and low, avidity T cells, as a biological consequence of T cell activation (1). Thus, at a biological system level, by specific recognition of the common target structures expressed on the intermediate avidity T cells, the immune system is able to achieve the goal of self non-self discrimination in the periphery by perceiving the avidity of T cell activation.

The biggest difficulty in transplant medicine is the reaction of the immune system to the foreign organ, termed rejection. Conventionally, recipients of a transplanted organ must indefinitely take immunosuppressive medications to fight rejection, which are both prone to failure and leave the patient at high risk of infection. The invention disclosed herein provides a novel treatment strategy of inducing permanent tolerance of the transplanted organ without long term use of immunosuppressive drugs which incorporates the avidity model.

SUMMARY OF THE INVENTION

A method for preventing rejection of a tissue transplanted from a donor subject into a recipient subject comprising:

a) administering to the recipient subject, prior to transplantation of the tissue, so as to inhibit activation of allo-reactive T cells in the recipient subject, (i) a plurality of peripheral blood mononuclear cells (PBMCs) from the donor subject, wherein the PBMCs have been irradiated such that they cannot proliferate in vivo, and (ii) a monoclonal antibody which specifically binds CD40 ligand, so as to inhibit activation of allo-reactive T cells in the recipient subject; and b) administering to the recipient subject, subsequent to transplantation of the tissue, an agent that enhances down-regulation of a donor tissue-activated HLA-E$^+$ T cell by an HLA-E-restricted CD8$^+$ T cell so as to thereby enhance down-regulation of the donor tissue-activated HLA-E$^+$ T cell, thereby preventing rejection of the tissue transplanted into the recipient subject.

BRIEF DESCRIPTION OF THE FIGURES

FIG. 1: The cellular events of Qa-1 (or HLA-E) restricted CD8+ T cell mediate pathway, initiated by the activation of naïve T cells during the primary immune response in which the TCRs on T cells interact with MHC/antigen peptide complexes presented by conventional APCs. One of the consequences of the initial T cell activation is the differential expression of a specific "target antigen", which, in this case, include the "Qa-1/self-peptide complex", on the surface of target T cells. Importantly, the expression of the "target antigen", which is recognized by the TCR on regulatory T cells, is determined by the avidity interactions of T cell activation, regardless of which antigen the target T cells are triggered by. In this regard, since T cells are not professional APCs, the professional APCs, such as dendritic cells may be recruited and function to provide co-stimulatory signals during the induction phase of the regulatory T cells. The "target antigen" expressed on certain activated T cells triggers the regulatory T cells to differentiate into effector cells, which in turn down-regulate any activated T cells expressing the same target antigen during the secondary immune response.

DETAILED DESCRIPTION OF THE INVENTION

A method for preventing rejection of a tissue transplanted from a donor subject into a recipient subject comprising:

a) administering to the recipient subject, prior to transplantation of the tissue, so as to inhibit activation of allo-reactive T cells in the recipient subject, (i) a plurality of peripheral blood mononuclear cells (PBMCs) from the donor subject, wherein the PBMCs have been irradiated such that they cannot proliferate in vivo, and (ii) a monoclonal antibody which specifically binds CD40 ligand, so as to inhibit activation of allo-reactive T cells in the recipient subject; and b) administering to the recipient subject, subsequent to transplantation of the tissue, an agent that enhances down-regulation of a donor tissue-activated HLA-E$^+$ T cell by an HLA-E-restricted CD8$^+$ T cell so as to thereby enhance down-regulation of the donor tissue-activated HLA-E$^+$ T cell, thereby preventing rejection of the tissue transplanted into the recipient subject.

A method for preventing rejection of a tissue transplanted from a donor subject into a recipient subject comprising:

a) administering to the recipient subject, prior to transplantation of the tissue, so as to inhibit activation of allo-reactive T cells in the recipient subject, (i) a plurality of peripheral blood mononuclear cells (PBMCs) from the donor subject, wherein the PBMCs have been irradiated such that they cannot proliferate in vivo, and (ii) a monoclonal antibody which specifically binds CD40 ligand, so as to inhibit activation of allo-reactive T cells in the recipient subject; and b) administering to the recipient subject, subsequent to transplantation of the tissue, an agent that enhances down-regulation of a donor tissue-activated HLA-E$^+$ T cell by an HLA-E-restricted CD8$^+$ T cell so as to thereby enhance down-regulation of the donor tissue-activated HLA-E$^+$ T cell, thereby preventing rejection of the tissue transplanted into the recipient subject.

In an embodiment, the method further comprises administering to the recipient subject an immunosuppressant pharmaceutical during step a), during step b) or during both step a) and step b).

In an embodiment, the agent is an HLA-E/IgG fusion protein or an HLA-E/Hsp60sp tetramer.

In an embodiment, the HLA-E$^+$ T cell is a CD4$^+$/HLA-E$^+$ T cell or a CD8$^+$/HLA-E$^+$ T cell.

In an embodiment, the agent is a dendritic cell-derived, HLA-E-bearing exosome loaded with a type B self peptide.

In an embodiment, the type B self peptide has the sequence set forth in SEQ ID NO:1.

In an embodiment, the agent is a dendritic cell-derived, HLA-E-bearing exosome loaded with Hsp60sp peptide.

In an embodiment, the agent is autologous dendritic T cells loaded with Hsp60sp peptide In an embodiment, the Hsp60sp peptide comprises consecutive amino acids having the sequence set forth in SEQ ID NO:2.

In an embodiment, the autologous dendritic T cells have been removed from the recipient subject, cultured ex vivo, and contacted with Hsp60sp peptide so as to load the cells with Hsp60sp peptide prior to the cells being administered as the agent to the recipient subject.

In an embodiment, the agent is administered intravenously, intramuscularly or orally.

In an embodiment, in step a) the monoclonal antibody directed against CD40 ligand is administered to the recipient subject for a period of up to 10 weeks.

In an embodiment, in step a) the plurality of cells from the donor subject is administered to the recipient subject in two separate portions, a first portion and then a second portion which is administered to the recipient subject about seven days after the first portion is administered.

In an embodiment, in step a) the monoclonal antibody directed against CD40 ligand is administered to the subject (1) on the day immediately prior to the day that the first portion of the plurality of cells is administered, and (2) on the day that the first portion of the plurality of cells is administered, and (3) on the day immediately after the day that the first portion of the plurality of cells is administered, and (4) three days after the first portion of the plurality of cells is administered, and (5) seven days after the first portion of the plurality of cells is administered, and (6) at 14, 21, 28, 35, 42, 49 and 56 days after the first portion of the plurality of cells is administered.

In an embodiment, the immunosuppressant pharmaceutical is administered daily for up to 10 weeks after administration of the plurality of cells, or first portion thereof, is administered.

In an embodiment, the immunosuppressant pharmaceutical agent is administered daily for 56 days.

In an embodiment, the tissue is transplanted into the recipient subject two to three weeks after administration of the plurality of cells, or first portion thereof.

In an embodiment, the method further comprises administering an anti-thromboembolic agent to the recipient subject during the period of administration of the monoclonal antibody directed against CD40 ligand.

In an embodiment, the transplanted tissue is lung tissue, heart tissue, kidney tissue, liver tissue, retinal tissue, corneal tissue, skin tissue, pancreatic tissue, intestinal tissue, genital tissue, ovary tissue, bone tissue, tendon tissue, or vascular tissue.

In an embodiment, the transplanted tissue is transplanted as an intact organ.

In an embodiment the PBMCs have been irradiated with 2000-4000 Rads for a sufficient amount of time such that they cannot proliferate in vivo.

As used herein a "recipient subject" is a subject who is to receive, or who has received, a transplanted cell, tissue or organ from another subject.

As used herein a "donor subject" is a subject from whom a cell, tissue or organ to be transplanted is removed before transplantation of that cell, tissue or organ to a recipient subject.

In an embodiment the donor subject is a primate. In a further embodiment the donor subject is a human. In an embodiment the recipient subject is a primate. In an embodiment the recipient subject is a human. In an embodiment both the donor and recipient subjects are human. Accordingly, the subject invention includes the embodiment of xenotransplantation.

As used herein "rejection by an immune system" describes the event of hyperactute, acute and/or chronic response of a recipient subject's immune system recognizing a transplanted cell, tissue or organ from a donor as non-self and the consequent immune response.

As used herein an "immunosuppressant pharmaceutical" is a pharmaceutically-acceptable drug used to suppress a recipient subject's immune response. Non-limiting examples include cyclosporine A, FK506 and rapamycine.

As used herein, a "prophylactically effective" amount is an amount of a substance effective to prevent or to delay the onset of a given pathological condition in a subject to which the substance is to be administered.

As used herein, a "therapeutically effective" amount is an amount of a substance effective to treat, ameliorate or lessen a symptom or cause of a given pathological condition in a subject suffering therefrom to which the substance is to be administered.

In one embodiment, the therapeutically or prophylactically effective amount is from about 1 mg of agent/kg subject to about 1 g of agent/kg subject per dosing. In another embodiment, the therapeutically or prophylactically effective amount is from about 10 mg of agent/kg subject to 500 mg of agent/subject. In a further embodiment, the therapeutically or prophylactically effective amount is from about 50 mg of agent/kg subject to 200 mg of agent/kg subject. In a further embodiment, the therapeutically or prophylactically effective amount is about 100 mg of agent/kg subject. In still a further embodiment, the therapeutically or prophylactically effective amount is selected from 50 mg of agent/kg subject, 100 mg of agent/kg subject, 150 mg of agent/kg subject, 200 mg of agent/kg subject, 250 mg of agent/kg subject, 300 mg of agent/kg subject, 400 mg of agent/kg subject and 500 mg of agent/kg subject. In the preferred embodiment the therapeutically or prophylactically effective amount is from about 20 mg of agent/kg subject per dosing.

As used herein a "type-B peptide" or "type-B self peptide" is a HLA-E-binding peptide that (i) does not inhibit NK cells by binding to CD94/NKG2A when bound to HLA-E, (ii) is recognized by regulatory CD8+ T cells when bound to HLA-E, and (iii) can compete with type-A HLA-E binding peptides, such as B7sp, for binding to HLA-E. Preferably, the type-B peptide is a nonomer.

As used herein "HLA-E" has the common meaning as used in the art, i.e. human leukocyte antigen system E.

As used herein a "HLA-E restricted CD8+ T cell" is a regulatory CD8+ T cell that recognizes the peptides presented by the HLA-E molecule on the immune system antigen presenting cells (APC) or on HLA-E+ dendritic cells. The APC for the HLA-E restricted CD8+ T cells as encompassed herein are intermediate avidity T cells, which are also specific targets for these CD8+ T cells.

"Structurally related peptide" with regard to Hsp60sp means a peptide having from 70% to 99% sequence similarity with the sequence set forth in SEQ ID NO:2.

As used herein "donor tissue-activated HLA-E$^+$ T cell" is a recipient's HLA-E$^+$ T cell which is activated by a donor tissue which has been transplanted into the recipient. Similarly, wherein the method, involves transplanted cells or organs, a "cell-activated HLA-E$^+$ T cell" or an "organ-activated HLA-E$^+$ T cell" is a recipient's HLA-E$^+$ T cell which is activated by a donor cell or organ, respectively, which has been transplanted into the recipient.

As used herein "allo-reactive T cell" is a T cell of a transplant recipient subject that reacts to donor subject cells wherein the donor is of the same species as the recipient. In an embodiment the allo-reactive T cell reacts to non-recipient human cells from a human donor, but does not react to recipient human cells.

In embodiments, the HLA-E$^+$ T cell is a CD4$^+$/HLA-E$^+$ T cell, a CD8$^+$/HLA-E$^+$ T cell, and the type B HLA-E binding peptide is Hsp60sp peptide. In a further embodiment the Hsp60sp peptide comprises consecutive amino acids having the sequence set forth in SEQ ID NO:2. In a further embodiment the peptide has the sequence Xaa-Met/Leu-Xaa-Xaa-Xaa-Xaa-Xaa-Xaa-Leu (SEQ ID NO:1). In a further embodiment the peptide is a nonomer which binds to HLA-E. In a further embodiment the peptide does not bind to the CD94/NKG2A receptor. In a further embodiment the peptide is recognized by the regulatory CD8+ T cells when bound to HLA-E. In a further embodiment the peptide can compete with B7sp for binding to HLA-E.

"Agent" shall mean any chemical entity, including, without limitation, a glycomer, a protein, an antibody, a lectin, a nucleic acid, a small molecule, and any combination thereof, as well as biological entities such as exosomes or liposomes. A "small molecule" is an organic molecule, which may be substituted with inorganic atoms or groups comprising inorganic atoms, which molecule has a molecular mass of less than 1000 Da. Specific non-limiting examples of agents include dendritic cell-derived, HLA-E-bearing exosome loaded with Hsp60sp peptide; autologous dendritic T cells loaded with Hsp60sp peptide; a membrane-bound composition or liposome loaded with Hsp60sp peptide; an HLA-E/IgG fusion protein; or an HLA-E/Hsp60sp tetramer. In embodiments the Hsp60sp peptide is a human Hsp60sp peptide.

In embodiments, the agent is a dendritic cell-derived HLA-E-bearing exosome loaded with type B HLA-E binding peptides, or the agent is a dendritic cell-derived, HLA-E-bearing exosome loaded with Hsp60sp peptide, or the agent is an HLA-E/IgG fusion protein, the agent is an HLA-E tetramer or an HLA-E/Hsp60sp tetramer. Fusion proteins are described in U.S. Pat. Nos. 5,116,964 and 5,336,603, which are hereby incorporated by reference. HLA-E tetramers are described in, for example, Braud et al., Nature. 1998 Feb. 19; 391(6669): 740-1, 743; and in Garcia et al., Eur. J. Immunol. 2002 April; 32(4):936-44, both of which are hereby incorporated by reference. HLA-E protein sequences are described by NCBI accession nos. CAA05527, CAA40172, BAB63328, and BAF31260, hereby incorporated by reference. In embodiments, the agent is a HLA-E/IgG fusion protein, the agent is a HLA-E tetramer or HLA-E/Hsp60sp tetramer. Tetramers are described in, for example, Salcedo et al., Eur. J. Immunol. 2000 April; 30(4):1094-101, which is hereby incorporated by reference. Agents suitable for use in the present invention are described in WO/2008/103471 published Aug. 28, 2008, which is hereby incorporated by reference.

Hsp60sp has the sequence QMRPVSRAL (SEQ ID NO:2) or for human is QMRPVSRVL (SEQ ID NO:3).

"Administering" an agent can be effected or performed using any of the various methods and delivery systems known to those skilled in the art. The administering can be performed, for example, intravenously, orally, nasally, via the cerebrospinal fluid, via implant, transmucosally, transdermally, intramuscularly, and subcutaneously. The following delivery systems, which employ a number of routinely used pharmaceutically acceptable carriers, are only representative of the many embodiments envisioned for administering compositions according to the instant methods.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropyl-methylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Span® series, Tween® series, and cetyl pyridine), preservatives and antioxidants (e.g., parabens, vitamins E and C, and ascorbic acid), anti-caking agents, coating agents, and chelating agents (e.g., EDTA).

As used herein, a "pharmaceutically acceptable carrier" is a pharmaceutically acceptable solvent, suspending agent or vehicle, for delivering the instant compounds to the animal or human. The carrier may be liquid, aerosol, gel or solid and is selected with the planned manner of administration in mind.

An "antibody" shall include, without limitation, an immunoglobulin molecule comprising two heavy chains and two light chains and which recognizes an antigen. The immunoglobulin molecule may derive from any of the commonly known classes, including but not limited to IgA, secretory IgA, IgG and IgM. IgG subclasses are also well known to those in the art and include but are not limited to human IgG1, IgG2, IgG3 and IgG4. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Methods for humanizing antibodies are well known to those skilled in the art. "Antibody" also includes, without limitation, a fragment or portion of any of the afore-mentioned immunoglobulin molecules and includes a monovalent and a divalent fragment or portion. Antibody fragments include, for example, Fc fragments and antigen-binding fragments (Fab).

"Monoclonal antibodies," also designated a mAbs, are antibody molecules whose primary sequences are essentially identical and which exhibit the same antigenic specificity. Monoclonal antibodies may be produced by hybridoma, recombinant, transgenic or other techniques known to those skilled in the art.

A "humanized" antibody refers to an antibody wherein some, most or all of the amino acids outside the CDR regions are replaced with corresponding amino acids derived from human immunoglobulin molecules. In one embodiment of the humanized forms of the antibodies, some, most or all of the amino acids outside the CDR regions have been replaced with amino acids from human immunoglobulin molecules, whereas some, most or all amino acids within one or more CDR regions are unchanged. Small additions, deletions, insertions, substitutions or modifications of amino acids are permissible as long as they do not abrogate the ability of the antibody to bind a given antigen. Suitable human immunoglobulin molecules include IgG1, IgG2, IgG3, IgG4, IgA, IgE and IgM molecules. A "humanized" antibody retains an antigenic specificity similar to that of the original antibody.

In an embodiment, the anti-CD40 ligand is the 5c8 monoclonal antibody, as produced by the 5c8 hybridoma, having ATCC Accession Number HB 10916, as described in U.S. Pat. No. 5,474,771, issued Dec. 12, 1995, which is hereby incorporated by reference in its entirety.

One skilled in the art would know how to make the humanized antibodies for use in the subject invention. Various publications, several of which are hereby incorporated by reference into this application, also describe how to make humanized antibodies. For example, the methods described in U.S. Pat. No. 4,816,567 comprise the production of chimeric antibodies having a variable region of one antibody and a constant region of another antibody.

U.S. Pat. No. 5,225,539 describes another approach for the production of a humanized antibody. This patent describes the use of recombinant DNA technology to produce a humanized antibody wherein the CDRs of a variable region of one immunoglobulin are replaced with the CDRs from an immunoglobulin with a different specificity such that the humanized antibody would recognize the desired target but would not be recognized in a significant way by the human subject's immune system. Specifically, site directed mutagenesis is used to graft the CDRs onto the framework.

Other approaches for humanizing an antibody are described in U.S. Pat. No. 5,585,089 (73) and U.S. Pat. No. 5,693,761 (74) and WO 90/07861 which describe methods for producing humanized immunoglobulins. These have one or more CDRs and possible additional amino acids from a donor immunoglobulin and a framework region from an accepting human immunoglobulin. These patents describe a method to increase the affinity of an antibody for the desired antigen. Some amino acids in the framework are chosen to be the same as the amino acids at those positions in the donor rather than in the acceptor. Specifically, these patents describe the preparation of a humanized antibody that binds to a receptor by combining the CDRs of a mouse monoclonal antibody with human immunoglobulin framework and constant regions. Human framework regions can be chosen to maximize homology with the mouse sequence. A computer model can be used to identify amino acids in the framework region which are likely to interact with the CDRs or the specific antigen and then mouse amino acids can be used at these positions to create the humanized antibody.

U.S. Pat. Nos. 5,585,089 and 5,693,761, and WO 90/07861 (75) also disclose four criteria which may used in designing the humanized antibodies. The first proposal was that for an acceptor, use a framework from a particular human immunoglobulin that is unusually homologous to the donor immunoglobulin to be humanized, or use a consensus framework from many human antibodies. The second proposal was that if an amino acid in the framework of the human immunoglobulin is unusual and the donor amino acid at that position is typical for human sequences, then the donor amino acid rather than the acceptor may be selected. The third proposal was that in the positions immediately adjacent to the 3 CDRs in the humanized immunoglobulin chain, the donor amino acid rather than the acceptor amino acid may be selected. The fourth proposal was to use the donor amino acid reside at the framework positions at which the amino acid is predicted to have a side chain atom within 3A of the CDRs in a three dimensional model of the antibody and is predicted to be capable of interacting with the CDRs. The above methods are merely illustrative of some of the methods that one skilled in the art could employ to make humanized antibodies. The affinity and/or specificity of the binding of the humanized antibody may be increased using methods of directed evolution as described in Wu et al. (1999) J. Mol. Biol. 284:151 and U.S. Pat. Nos. 6,165,793; 6,365,408 and 6,413,774.

Hsp60sp has the sequence QMRPVSRAL (SEQ ID NO:2) or for human is QMRPVSRVL (SEQ ID NO:3).

All combinations of the various elements of methods, compositions and processes described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

The Avidity Model emphasizes that selective down-regulation of intermediate avidity T cells specific to any antigens, in the context of a truncated T cell repertoire devoid of high avidity T cells, is the biological basis that the immune system employs to achieve peripheral self-tolerance. Based on this property of the regulatory system, normally acute graft rejection is mediated by the allo-reactive T cells of high avidity that are resistant to down-regulation, whereas chronic graft rejection is mediated predominately by allo-reactive T cells of intermediate avidity that are subject to down-regulation. Here it is disclosed that either deleting high avidity allo-reactive T cells or converting the allo-reactive T cells from high avidity to intermediate avidity by employing agents know to decrease the avidity of T cells responding to allo-antigens. The resulting allo-reactive T cell repertoire would then be devoid of high avidity but enriched in intermediate avidity allo-reactive T cells which would induce regulatory suppressor cells and also be susceptible to the suppression.

Certain currently used non-specific immunosuppressive agents employed to prevent acute graft rejection will reshape the T cell repertoire to the graft by preferentially irradiating the most activated clones, which are likely to be of high avidity and thus enrich in intermediate avidity T cells. This would place the transplanted graft in a unique position between a foreign antigen and a self-antigen with respect of the composition of the allo-responding T cell repertoire. Based on the Avidity Model, this creates a situation that enables the immune system to treat the graft as if it were a self-antigen. For example, the graft may survive the acute rejection by use of immuno-modulatory agents, such as "anti-CD40L mAb", which could specifically modify the allo-reactive T cell repertoire by eliciting an intermediate avidity response, which is lacking high avidity allo-reactive T cells. The residual allo-reactive T cells may mainly mediate the subsequent chronic rejection with intermediate avidity that is constantly being activated by the accepted graft in vivo. An effective approach to down-regulate these cells would be to re-activate the HLA-E restricted CD8+ T cell mediated regulatory pathway, which may have been impaired by the prior anti-rejection treatment during the acute rejection phase.

In this regard, the anti-CD40L mAb 5C8 has been shown, in non-human primates, to induce long-term transplantation tolerance following relatively short-term treatment of allograft rejection (20-24). Indeed, a single course of therapy over a one-month period of time has resulted in allograft tolerance for several years. Induction of drug free long-term tolerance is due, in part, to the modification of allo-reactive T cell repertoire by the initial exposure to anti-CD40L therapy, which allows the selective down-regulation of intermediate avidity allo-reactive T cells by the HLA-E restricted regulatory CD8+ T cells. However, the use of anti-CD40L mAb to treat immunologically related clinical problems has been held in abeyance because the drug is known to have the side effect of inducing thromboembolic phenomenon in a small but significant percentage of patients over time. In this regard, the Avidity Model provides a theoretical basis for a one-time use of anti-CD40L to modify the allo-reactive T cell repertoire in combination with subsequent re-activation of HLA-E restricted CD8+ T cell regulatory pathway to establish a permanent transplantation tolerance. One-time use of anti-CD40L mAb could significantly reduce the probability of thromboembolic phenomenon and also allow the patients to be closely monitored during administration of anti-CD40L in the hospital. Moreover, short-term therapeutic regimen allows use of anti-thrombotic therapy including aspirin and anti-platelet drug Plavix® commonly employed to prevent thromboembolism. For example anti-platelet drug used during the insertion of cardiac stents for myocardial insufficiency could be similarly employed to prevent thromboembolic complication in anti-CD40L mAb therapy.

A protocol of induction of transplantation tolerance is as follows. The treatment is composed of two stages: a one-time (a few weeks) use of anti-CD40L mAb in combination with immuno-suppressing drugs during donor specific transfusion (DST) to modify the anti-allo T cell repertoire followed by re-activation of HLA-E restricted CD8+ T cells.

Stage 1. Modification of the Allo-Reactive Repertoire and to Eliminate High Avidity Anti-Donor Specific T Cells.

DST is designed to elicit a primary anti-allo immune response to provide a time window for modification of the allo-reactive T cell repertoire to eliminate high avidity allo-reactive T cells before graft transplantation. DST is accomplished by injecting recipients with $10\times10^6$ irradiated donor cells (PBMC from human or monkey) intravenously on day 1, and day 7 as a boost. Anti CD40L mAb will be injected into recipients at 20 mg/kg on days −1, 0, 3, 7 and weekly for 8 weeks (25). The immuno-suppressive drugs (including Cyclosporine A, FK506 or Rapamycine) will be administrated in 8 weeks as routinely used for the transplantation patients. The graft transplantation (the secondary anti-allo response) will be performed 2-3 weeks after the beginning of the treatment.

During administration of anti-CD40L, anti-platelet drug Plavix® and Aspirin will be given to the recipients, and the recipients will be required to be hospitalized and monitored closely for any sign of thromboembolic complications.

Stage 2. Induction of HLA-E Restricted CD8+ T Cell Pathway to Prevent Chronic Rejection.

The second stage should follow the completion of the first stage. The following agents can be administrated to the patients:

1. HLA-E tetramer: HLA-E-Hsp60sp tetramer can be used as specific antigen to induce HLA-E restricted CD8+ T cells in vivo.

2. Exosome: HLA-E bearing exosomes loaded with HLA-E binding peptides of choice can be used to activate this pathway in vivo (26). It is well established that dendritic cell-derived exosomes which bear functional MHC class I and class II molecules that can be loaded with synthetic peptides of choice can be used as a peptide-based vaccines (26).

3. A molecularly-engineered complex composed of HLA-E/Hsp60sp could also be used as an antigen to specifically activate HLA-E restricted CD8+ T cells. In this regard, it is known that MHC-multimers can be valuable tools for both the stimulation of as well as the analysis of antigen specific T cells in immune response as part of an artificial antigen presenting cells (27-32).

4. Vaccination of recipients with autologous dendritic T cells loaded with Hsp60sp.

To load cells with Hsp60sp., e.g. recipient dendritic cells, the cells, from, e.g. PBMC, are cultured in vitro for 6 days and then loaded with Hsp60sp at 50 uM, 37° C. for two hours and then administrated into the recipients intravenously.

By inducing tolerance to the donor tissue, the technology reduces or eliminates the need for continuous immunosuppressive therapy.

Example

Before an organ is transplanted into a recipient subject, to the subject is administered (i) a plurality of cells from the donor subject, wherein the donor cells have been irradiated, and (ii) a monoclonal antibody which specifically binds CD40 ligand, so as to inhibit activation of allo-reactive T cells in the recipient subject. The transplant surgery is performed on the subject. After the transplantation an agent that enhances down-regulation of a donor tissue-activated HLA-E$^+$ T cell by an HLA-E-restricted CD8$^+$ T cell is administered to the recipient subject, thereby enhancing down-regulation of the donor tissue-activated HLA-E$^+$ T cell, so as to thereby prevent rejection by the immune system of the recipient subject of the tissue transplanted into the recipient subject. In a further example the recipient subject is further administered an immunosuppressant pharmaceutical.

REFERENCES

1. Chen, W., L. Zhang, B. Liang, Y. Saenger, J. Li, L. Chess, and H. Jiang. 2007. Perceiving the avidity of T cell activation can be translated into peripheral T cell regulation. Proc Natl Acad Sci USA 104:20472-20477.
2. Burnet, M., and F. Fenner. 1949. Production of Antibodies. McMillan, Melbourne.
3. Billingham, R. E., L. Brent, and P. B. Medawar. 1953. Actively acquired tolerance of foreign cells. Nature 172:603-606.
4. Bevan, M. J. 1977. In a radiation chimaera, host H-2 antigens determine immune responsiveness of donor cytotoxic cells. Nature 269:417-418.
5. Waldmann, H. 1978. The influence of the major histocompatibility complex on the function of T-helper cells in antibody formation. Immunol Rev 42:202-223.
6. Zinkernagel, R. M. 1978. Thymus and lymphohemopoietic cells: their role in T cell maturation in selection of T cells' H-2-restriction-specificity and in H-2 linked Ir gene control. Immunol Rev 42:224-270.
7. von Boehmer, H., and P. Kisielow. 1990. Self-nonself discrimination by T cells. Science 248:1369-1373.
8. Kappler, J. W., N. Roehm, and P. Marrack. 1987. T cell tolerance by clonal elimination in the thymus. Cell 49:273-280.
9. Hengartner, H., B. Odermatt, R. Schneider, M. Schreyer, G. Walle, H. R. MacDonald, and R. M. Zinkernagel. 1988. Deletion of self-reactive T cells before entry into the thymus medulla. Nature 5(336):388-390.
10. Pircher, H., U. H. Rohrer, D. Moskophidis, R. M. Zinkernagel, and H. Hengartner. 1991. Lower receptor avidity required for thymic clonal deletion than for effector T-cell function. Nature 351:482-485.
11. Bouneaud, C., P. Kourilsky, and P. Bousso. 2000. Impact of negative selection on the T cell repertoire reactive to a self-peptide: a large fraction of T cell clones escapes clonal deletion. Immunity 13:829-840.
12. Sandberg, J. K., L. Franksson, J. Sundback, J. Michaelsson, M. Petersson, A. Achour, R. P. Wallin, N. E. Sherman, T. Bergman, H. Jornvall, D. F. Hunt, R. Kiessling, and K. Karre. 2000. T cell tolerance based on avidity thresholds rather than complete deletion allows maintenance of maximal repertoire diversity. J Immunol 165:25-33.
13. Jiang, H., S. Curran, E. Ruiz-Vazquez, B. Liang, R. Winchester, and L. Chess. 2003. Regulatory CD8+ T cells fine-tune the myelin basic protein-reactive T cell receptor V beta repertoire during experimental autoimmune encephalomyelitis. Proc Natl Acad Sci USA 100:8378-8383. Epub 203 June 8324.
14. Anderton, S. M., C. G. Radu, P. A. Lowrey, E. S. Ward, and D. C. Wraith. 2001. Negative selection during the peripheral immune response to antigen. J Exp Med 193:1-11.
15. Han, B., P. Serra, J. Yamanouchi, A. Amrani, J. F. Elliott, P. Dickie, T. P. Dilorenzo, and P. Santamaria. 2005. Developmental control of CD8 T cell-avidity maturation in autoimmune diabetes. J Clin Invest 115:1879-1887.
16. Zehn, D., and M. J. Bevan. 2006. T cells with low avidity for a tissue-restricted antigen routinely evade central and peripheral tolerance and cause autoimmunity. Immunity 25:261-270.

17. Jiang, H., and L. Chess. 2006. Regulation of immune responses by T cells. N Engl J Med 354:1166-1176.
18. Jiang, H., and L. Chess. 2000. The Specific Regulation of Immune Responses by CD8+ T Cells Restricted by the MHC Class IB Molecule, QA-1. Annu. Rev. Immunol. 18:185-216.
19. Jiang, H., Y. Wu, B. Liang, Z. Zheng, G. Tang, J. Kanellopoulos, M. Soloski, R. Winchester, I. Goldstein, and L. Chess. 2005. An affinity/avidity model of peripheral T cell regulation. J. Clin. Invest. 115:302-312.
20. Durie, F. H., T. M. Foy, S. R. Masters, J. D. Laman, and R. J. Noelle. 1994. The role of CD40 in the regulation of humoral and cell-mediated immunity. [Review]. Immunology Today 15:406-411.
21. Blazar, B. R., P. A. Taylor, A. Panoskaltsis-Mortari, J. Buhlman, J. Xu, R. A. Flavell, R. Korngold, R. Noelle, and D. A. Vallera. 1997. Blockade of CD40 ligand-CD40 interaction impairs CD4+ T cell-mediated alloreactivity by inhibiting mature donor T cell expansion and function after bone marrow transplantation. J Immunol 158:29-39.
22. Kirk, A. D., D. M. Harlan, N. N. Armstrong, T. A. Davis, Y. Dong, G. S. Gray, X. Hong, D. Thomas, J. Fechner, Jr., and S. J. Knechtle. 1997. CTLA4-Ig and anti-CD40 ligand prevent renal allograft rejection in primates. Proc Natl Acad Sci USA 94:8789-8794.
23. Chess, L. 2000. Blockade of the CD40L/CD40 Pathway. In Therapeutic Immunology, 2nd ed. K. F. Austen, S. J. Burakoff, F. S. Rosen, and T. B. Strom, eds. Blackwell Science, Inc., Cambridge, Mass.
24. Honey, K., S. P. Cobbold, and H. Waldmann. 1999. CD40 ligand blockade induces CD4+ T cell tolerance and linked suppression. J Immunol 163:4805-4810.
25. Preston, E. H., H. Xu, K. K. Dhanireddy, J. P. Pearl, F. V. Leopardi, M. F. Starost, D. A. Hale, and A. D. Kirk. 2005. IDEC-131 (anti-CD154), sirolimus and donor-specific transfusion facilitate operational tolerance in non-human primates. Am J Transplant 5:1032-1041.
26. Chaput, N., N. E. Schartz, F. Andre, J. Taieb, S. Novault, P. Bonnaventure, N. Aubert, J. Bernard, F. Lemonnier, M. Merad, G. Adema, M. Adams, M. Ferrantini, A. F. Carpentier, B. Escudier, T. Tursz, E. Angevin, and L. Zitvogel. 2004. Exosomes as potent cell-free peptide-based vaccine. II. Exosomes in CpG adjuvants efficiently prime naive Tc1 lymphocytes leading to tumor rejection. J Immunol 172: 2137-2146.
27. Dal Porto, J., T. E. Johansen, B. Catipovic, D. J. Parfiit, D. Tuveson, U. Gether, S. Kozlowski, D. T. Fearon, and J. P. Schneck. 1993. A soluble divalent class I major histocompatibility complex molecule inhibits alloreactive T cells at nanomolar concentrations. Proc Natl Acad Sci USA 90:6671-6675.
28. Oelke, M., and J. P. Schneck. 2004. HLA-Ig-based artificial antigen-presenting cells: setting the terms of engagement. Clin Immunol 110:243-251.
29. Casares, S., C. A. Bona, and T. D. Brumeanu. 1997. Engineering and characterization of a murine MHC class II-immunoglobulin chimera expressing an immunodominant CD4 T viral epitope. Protein Eng 10:1295-1301.
30. Malherbe, L., C. Filippi, V. Julia, G. Foucras, M. Moro, H. Appel, K. Wucherpfennig, J. C. Guery, and N. Glaichenhaus. 2000. Selective activation and expansion of high-affinity CD4+ T cells in resistant mice upon infection with *Leishmania major*. Immunity 13:771-782.
31. Casares, S., C. A. Bona, and T. D. Brumeanu. 2001. Enzymatically mediated engineering of multivalent MHC class II-peptide chimeras. Protein Eng 14:195-200.
32. Altman, J. D., P. A. Moss, P. J. Goulder, D. H. Barouch, M. G. McHeyzer-Williams, J. I. Bell, A. J. McMichael, and M. M. Davis. 1996. Phenotypic analysis of antigen-specific T lymphocytes. Science 274:94-96.

What is claimed is:

1. A method for preventing rejection of a tissue transplanted from a donor subject into a recipient subject comprising:
   a) administering to the recipient subject, prior to transplantation of the tissue, (i) a plurality of peripheral blood mononuclear cells (PBMCs) from the donor subject, wherein the PBMCs have been irradiated and do not proliferate in vivo, and (ii) an anti-CD40 ligand (anti-CD40L) antibody; and
   b) administering to the recipient subject, subsequent to transplantation of the tissue, (i) dendritic cells loaded with a type B self peptide, or (ii) a membrane-bound, HLA-E-bearing composition loaded with a type B peptide,
      wherein the type B self peptide comprises the amino acid sequence set forth in SEQ ID NO: 1.

2. The method of claim 1, further comprising administering to the recipient subject an immunosuppressant pharmaceutical during step a).

3. The method of claim 1, wherein the type B self peptide is Hsp60sp peptide comprising the amino acid sequence set forth in SEQ ID NO: 2 or in SEQ ID NO: 3.

4. The method of claim 3, wherein the dendritic cells loaded with Hsp60sp peptide are prepared by removing autologous dendritic cells from the recipient subject, culturing the autologous dendritic cells ex vivo, and loading the autologous dendritic cells with Hsp60sp peptide.

5. The method of claim 1, wherein the dendritic cells or the membrane-bound, HLA-E-bearing composition are administered intravenously, subcutaneously, intramuscularly or orally.

6. The method of claim 1, wherein in step a) the anti-CD40L antibody is administered to the recipient subject for a period of up to 10 weeks.

7. The method of claim 1, wherein in step a) the plurality of PBMCs from the donor subject is administered to the recipient subject optionally in two separate portions, a first portion 2 to 3 weeks before transplantation, and then optionally a second portion which is administered to the recipient subject about seven days after the first portion is administered.

8. The method of claim 2, wherein the immunosuppressant pharmaceutical is cyclosporine A, FK506 or rapamycin.

9. The method of claim 7, wherein an immunosuppressant pharmaceutical is administered daily for up to 10 weeks after administration of the plurality of PBMCs, or first portion thereof.

10. The method of claim 7, wherein the tissue is transplanted into the recipient subject two to three weeks after administration of the plurality of PBMCs or first portion thereof.

11. The method of claim 1, further comprising administering an anti-thromboembolic agent to the recipient subject during the period of administration of the anti-CD40L antibody.

12. The method of claim 1, wherein the transplanted tissue is lung tissue, heart tissue, kidney tissue, liver tissue, retinal tissue, corneal tissue, skin tissue, pancreatic tissue, intestinal tissue, genital tissue, ovary tissue, bone tissue, tendon tissue, or vascular tissue.

13. The method of claim 1, wherein the transplanted tissue is an intact organ.

* * * * *

UNITED STATES PATENT AND TRADEMARK OFFICE
CERTIFICATE OF CORRECTION

| | | |
|---|---|---|
| PATENT NO. | : 9,155,787 B2 | Page 1 of 1 |
| APPLICATION NO. | : 14/540452 | |
| DATED | : October 13, 2015 | |
| INVENTOR(S) | : Hong Jiang et al. | |

It is certified that error appears in the above-identified patent and that said Letters Patent is hereby corrected as shown below:

In the Specification

In column 1, line 38, before "Background", insert -- This invention was made with government support under AI046132 awarded by the National Institutes of Health. The government has certain rights in the invention. --.

Signed and Sealed this
Third Day of May, 2016

Michelle K. Lee
*Director of the United States Patent and Trademark Office*